(12) United States Patent
Miyazato et al.

(10) Patent No.: US 9,233,122 B2
(45) Date of Patent: Jan. 12, 2016

(54) AGENT FOR SUPPRESSING ELEVATION OF BLOOD ALCOHOL CONCENTRATION

(71) Applicant: MATSUTANI CHEMICAL INDUSTRY CO., LTD., Itami-shi, Hyogo (JP)

(72) Inventors: Shoko Miyazato, Itami (JP); Yuka Kishimoto, Sanda (JP)

(73) Assignee: MATSUTANI CHEMICAL INDUSTRY CO., LTD., Hyogo (JP)

( * ) Notice: Subject to any disclaimer, the term of this patent is extended or adjusted under 35 U.S.C. 154(b) by 9 days.

(21) Appl. No.: 13/711,225

(22) Filed: Dec. 11, 2012

(65) Prior Publication Data

US 2013/0157975 A1    Jun. 20, 2013

(30) Foreign Application Priority Data

Dec. 15, 2011    (JP) ................................ 2011-274820

(51) Int. Cl.
  *A61K 31/716*    (2006.01)
  *A61K 31/718*    (2006.01)
  *A23L 1/09*    (2006.01)

(52) U.S. Cl.
  CPC .............. *A61K 31/716* (2013.01); *A23L 1/095* (2013.01); *A61K 31/718* (2013.01); *A23V 2002/00* (2013.01)

(58) Field of Classification Search
  None
  See application file for complete search history.

(56) References Cited

U.S. PATENT DOCUMENTS

| | | | |
|---|---|---|---|
| 3,956,511 A * | 5/1976 | Mitchell et al. | 426/106 |
| 4,594,249 A * | 6/1986 | Procter et al. | 424/125 |
| 2008/0020995 A1 * | 1/2008 | Purpura et al. | 514/58 |
| 2009/0004326 A1 * | 1/2009 | Andrews | 426/2 |
| 2013/0017276 A1 * | 1/2013 | Blackman | 424/717 |

FOREIGN PATENT DOCUMENTS

| | | |
|---|---|---|
| JP | 06-014751 A | 1/1994 |
| JP | 07-053385 A | 2/1995 |
| JP | 08-277221 A | 10/1996 |
| JP | 11-228428 A | 8/1999 |
| JP | 2001-226277 A | 8/2001 |
| JP | 2002-193823 A | 7/2002 |
| JP | 2005-021006 A | 1/2005 |
| JP | 2007-332277 A | 12/2007 |
| JP | 2008-524124 A | 7/2008 |
| JP | 2010-115124 A | 5/2010 |
| KR | 10-2005-0029898 A | 3/2005 |
| KR | 10-2008-0105510 A | 12/2008 |
| WO | 2006/106704 A1 | 10/2006 |
| WO | 2007/023931 A1 | 3/2007 |

OTHER PUBLICATIONS

Sankaran et al., "Enteral Macronutrients Abolish High Blood Alcohol Levels in Chronic Alcoholic Rats," Nutrition Research, 1991, vol. 11, No. 2-3, pp. 217-222.
European Patent Office, European Search Report issued in corresponding EP Application No. 12196867.1, dated Mar. 11, 2013.
Hajime et al., "Application of modified starch and dextrin for carbonated beverages", Food Chemical, 2010, vol. 26, No. 11, pp. 71-73 (9 pages total).
Japan Patent Office, Communication dated Sep. 16, 2015, issued in corresponding Japanese Application No. 2011-274820.

* cited by examiner

*Primary Examiner* — Layla Bland
(74) *Attorney, Agent, or Firm* — Sughrue Mion, PLLC

(57) ABSTRACT

An object of the present invention is to provide an agent for suppressing elevation of blood alcohol concentration and a method for suppressing elevation of blood alcohol concentration, the agent and the method enabling prevention of an intoxication state upon drinking and further prevention of hepatic dysfunctions due to drinking such as fatty liver. Provided are an agent for suppressing elevation of blood alcohol concentration, comprising a dextrin as an active ingredient, and a method for suppressing elevation of blood alcohol concentration, comprising, when alcohol is ingested, ingesting 0.5 parts by mass or more of a digestible dextrin and/or an indigestible dextrin relative to 1 part by mass of the ingested alcohol.

2 Claims, 2 Drawing Sheets

AGENT FOR SUPPRESSING ELEVATION OF BLOOD ALCOHOL CONCENTRATION

TECHNICAL FIELD

The present invention relates to an agent and a method for suppressing rapid elevation of blood alcohol concentration upon ingestion of an alcoholic beverage.

BACKGROUND ART

When alcohol is ingested excessively, acute and chronic poisoning symptoms are often observed. Hence, various studies have conventionally been made in search of specific medicines for preventing intoxication, accelerating sobering-up, and preventing alcoholism. In particular, various substances including very traditional ones have been proposed for preventing intoxication and accelerating sobering-up.

For example, fructose, which is contained in fruits in large amounts, glucose, Kaki persimmon fruit extract, organic acids, sodium acetate, yeast cells, ω6 unsaturated fatty acids, carnitine chloride, *Panax japonicus, Eleutherococcus senticosus*, and the like have been proposed so far as agents for preventing intoxication or preventing getting sick from drinking.

Moreover, for example, Patent Literature 1 discloses a composition for inhibiting alcohol absorption, comprising a dried product of sake lees obtained by brewing of sake. Patent Literature 2 discloses an agent for inhibiting alcohol absorption, comprising caffeine as an active ingredient. Patent Literature 3 discloses an agent for inhibiting alcohol absorption, comprising at least one of glycosides in which the sapogenin is oleanolic acid, glycosides in which the sapogenin is presenegenin, glycosides in which the sapogenin is hederagenin, and glycosides in which the sapogenin is protoescigenin. Patent Literature 4 discloses a beverage for inhibiting elevation of blood alcohol concentration, comprising glycerol as an active ingredient for inhibiting elevation of blood alcohol concentration. Patent Literature 5 discloses a composition for suppressing elevation of blood alcohol concentration, comprising a basic amino acid or a salt thereof as an active ingredient. Patent Literature 6 discloses a composition for improving blood alcohol metabolism, comprising as an active ingredient a peptide mixture which is obtained by enzymatically degrading soybean protein and which has an average molecular weight of 500 to 15000. Patent Literature 7 discloses an agent for controlling absorption and metabolism of alcohol, comprising a processed soybean product as an active ingredient. Patent Literature 8 discloses a composition for a food or beverage which is intended to decrease blood alcohol concentration, comprising a fermentation product obtained by fermentation of brown sugar as an ingredient.

However, only a few of the above-described conventional technologies have been put into practical use, because the effects of the technologies are insufficient, or the administration as beverage is difficult.

CITATION LIST

Patent Literature

[Patent Literature 1] Japanese Patent Application Publication No. Hei 11-228428
[Patent Literature 2] Japanese Patent Application Publication No. Hei 08-277221
[Patent Literature 3] Japanese Patent Application Publication No. Hei 07-053385
[Patent Literature 4] Japanese Patent Application Publication No. Hei 06-014751
[Patent Literature 5] WO2007-023931
[Patent Literature 6] WO2006-106704
[Patent Literature 7] Japanese Patent Application Publication No. 2001-226277
[Patent Literature 8] Japanese Patent Application Publication No. 2010-115124

SUMMARY OF INVENTION

Technical Problems

The present invention is to provide a substance for suppressing elevation of blood alcohol concentration upon drinking, the substance being safer and easier to administer. The present invention is to provide an agent for suppressing elevation of blood alcohol concentration and the use thereof, the agent and the use enabling prevention of an intoxication state upon drinking and further prevention of hepatic dysfunctions due to drinking such as fatty liver.

Solution to Problems

The present inventors have earnestly studied food materials for preventing intoxication upon drinking. As a result, the present inventors have found that dextrins, especially indigestible dextrins, remarkably lower blood alcohol concentration after drinking. This finding and further subsequent studies have led to the completion of the present invention. Specifically, the present invention relates to an agent for suppressing elevation of blood alcohol concentration, comprising a dextrin, especially a digestible dextrin or an indigestible dextrin, as an active ingredient. Moreover, the present invention provides a method for suppressing elevation of blood alcohol concentration, comprising, when an alcoholic beverage is ingested, ingesting a dextrin in an amount which is a half or more of the amount of the ingested alcohol.

Advantageous Effects of Invention

The present invention makes it possible to provide an agent for suppressing elevation of blood alcohol concentration and a method for suppressing elevation of blood alcohol concentration, the agent and the method being capable of suppressing sudden elevation of blood alcohol concentration after ingestion of an alcoholic beverage, and being safe and easy to administer. The suppressing agent and the suppressing method enable prevention of an intoxication state upon drinking and, in a medium- and long-term perspective, enable healthy drinking, which may leads to prevention of hepatic dysfunctions due to drinking such as fatty liver.

DESCRIPTION OF EMBODIMENTS

Figure 1:
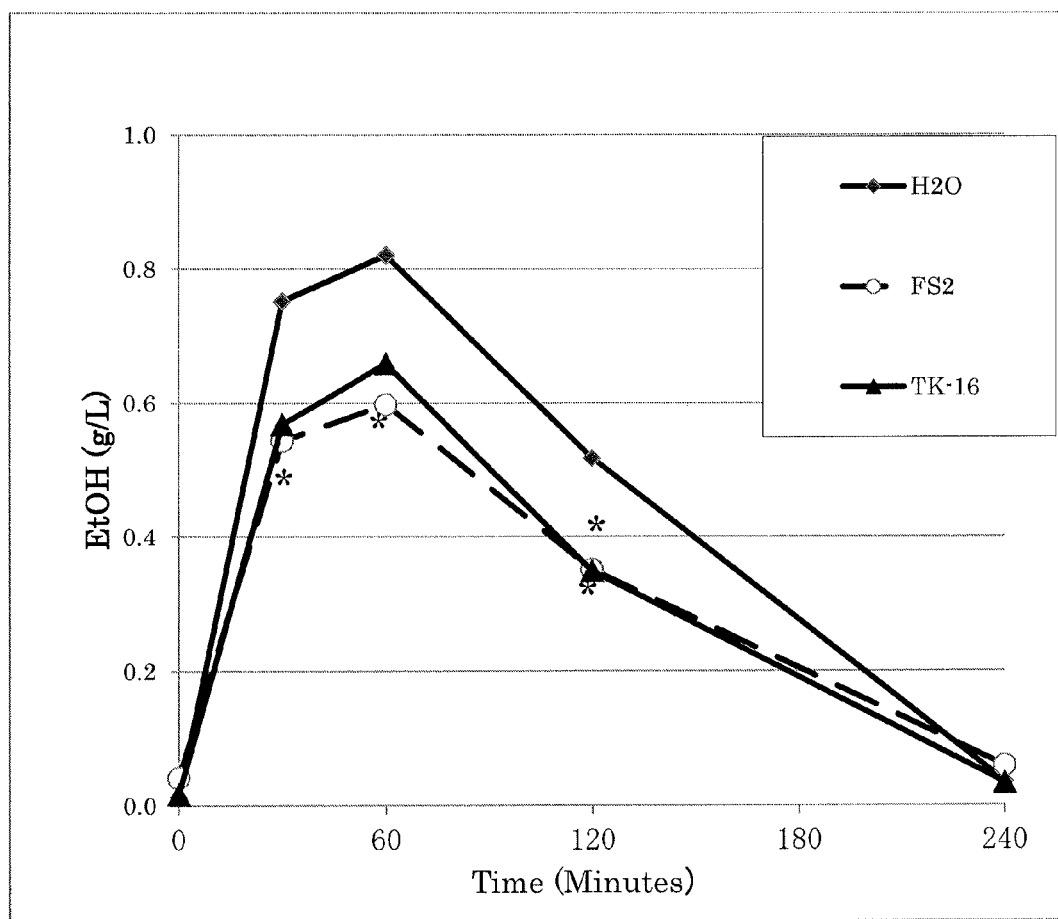
FIG. 1 shows the change in blood ethanol concentration after purified water ($H_2O$), a 40% dextrin (TK-16) solution, or a 40% indigestible dextrin (FS2) solution, and the same amount of a 40% aqueous ethanol solution were administered to rats. * indicates that the value is significant over that of purified water.

The term "dextrin" herein is a generic term for starch degradation products and pyrodextrin degradation products obtained by degradation of starches or pyrodextrins with an acid or an amylolytic enzyme such as an amylase, and derivatives thereof. The term "dextrin" encompasses pyrodextrins, digestible dextrins, indigestible dextrins, and hydrogenated products thereof.

The digestible dextrins are starch degradation products obtained by degradation of starches with an acid or an amylolytic enzyme such as amylase. The indigestible dextrins are non-digestible dextrins obtained by degradation of pyrodextrins with an acid or an amylolytic enzyme such as amylase. The hydrogenated products of digestible dextrins or indigestible dextrins mean those obtained by catalytic reduction in which these digestible dextrins or indigestible dextrins are brought into contact with hydrogen gas under a pressurized condition in the presence of a metal catalyst.

The pyrodextrins used for producing dextrins are dextrins which are dry-heat degradation products of starch obtained by heating a starch to a temperature in the range from 120 to 200° C. in the presence of an inorganic acid such as hydrochloric acid or an organic acid such as oxalic acid and which contain a small amount of non-digestible components.

More specifically, the pyrodextrins are obtained by adding, to a starch, a mineral acid (for example, hydrochloric acid, nitric acid, or sulfuric acid), preferably hydrochloric acid, for example, 3 to 10% by mass of a 1% by mass aqueous hydrochloric acid solution relative to 100 parts by mass of the starch, followed by a heat treatment. It is preferable that, in order to uniformly mix the aqueous solution of the starch and the mineral acid, the aqueous solution be stirred, and aged (for several hours) in an appropriate mixer before the heat treatment, and then the water content in the mixture be reduced to about 5% by mass by preliminary drying at about preferably 100 to 120° C. It is appropriate to conduct the heat treatment at 120 to 200° C., and preferably 150 to 200° C. for 10 to 120 minutes, and preferably 30 minutes to 120 minutes. The higher the heat treatment temperature, the higher the content of indigestible components in the target product. However, since colored substances tend to be formed at 180° C. or higher, the heat treatment temperature is more preferably 150 to 180° C.

The acid used in the degradation of a starch or a pyrodextrin with an acid during the production of a digestible dextrin or a non-digestible dextrin may be an organic acid (for example, oxalic acid or citric acid) or an inorganic acid (for example, hydrochloric acid, nitric acid, or sulfuric acid), and is preferably hydrochloric acid, oxalic acid, or the like, and further preferably hydrochloric acid.

In general, wet degradation is employed for the production of a digestible dextrin. A more specific production method is as follows. A starch is suspended in water at a concentration of 20 to 40%, and the pH is adjusted to 5.5 to 6.5 with calcium carbonate or oxalic acid. Then, an α-amylase is added thereto in an amount of 0.05 to 0.3% by mass relative to the solid content, and the starch is liquefied by hydrolysis conducted at a heating temperature of 80 to 100° C. for about 30 to 60 minutes. Subsequently, the enzymatic reaction is stopped by applying a pressure of about 0.2 MPa, or by adding an acid such as oxalic acid. Then the liquid in which the reaction is stopped is purified, concentrated, and dried to obtain a product.

A more specific method for producing an indigestible dextrin is as follows. An aqueous solution containing a pyrodextrin at about 20 to 45% by mass is prepared, and the pH of the aqueous pyrodextrin solution is adjusted to 5.5 to 6.5. Then, an α-amylase is added thereto, for example, in an amount of 0.05 to 0.2% by mass relative to the pyrodextrin in the case of Termamyl 60L (product name, manufactured by Novo Nordisk Bioindustries). When other α-amylase is used, an equivalent amount of the α-amylase may be added depending on the potency of the enzyme. After the addition of the α-amylase, the solution is heated to carry out hydrolysis at 85 to 100° C., at which the α-amylase acts, (the temperature varies depending on the kind of α-amylase) for 30 minutes to 2 hours. Subsequently, the temperature is elevated to about 120° C. (the inactivation temperature of the α-amylase) to stop the action of the α-amylase. At this time, the pH may be lowered to a value at which the α-amylase is inactivated, i.e., about pH 4 by adding an acid such as hydrochloric acid or oxalic acid.

The digestible dextrin or the indigestible dextrin may be used after being subjected to a catalytic reduction by being brought into contact with hydrogen gas in the presence of a metal catalyst such as Raney nickel under the conditions of 80 to 120 kg/cm$^2$ and 120 to 140° C.

Examples of the dextrins include commercially available dextrins such as TK-16, Pinedex #1, Pinedex #2, Fibersol 2, and Fibersol 2H (these are manufactured by Matsutani Chemical Industry Co., Ltd.) and NUTRIOSE (manufactured by Roquette).

Alternatively, the dextrin in the present invention may be a synthetic dextrin derivative having a structure and functions similar to those of dextrin, for example, polydextrose available from Danisco Japan Ltd.

The term "dextrin derivative" herein means those obtained by chemically or enzymatically processing dextrins, and encompasses, for example, branched dextrins obtained by causing a glycosyltransferase to act on a dextrin, and cyclodextrins obtained by causing a cyclodextrin producing enzyme to act on a starch, in addition to the above-described polydextrose.

Typical dextrins used for the agent and method for suppressing elevation of blood alcohol concentration of the present invention include digestible dextrins and indigestible dextrins. From the viewpoint of effects, indigestible dextrins are further preferable. It is also possible to use a digestible dextrin and an indigestible dextrin in combination. In this case, the content of the indigestible dextrin in the dextrins is preferably at least 80% by mass, and more preferably 90% by mass or more.

One of or a combination of two or more of those dextrins can be used as the agent for suppressing elevation of blood alcohol concentration of the present invention. Further, the agent for suppressing elevation of blood alcohol concentration of the present invention can be used in combination with another compound having an effect of suppressing elevation of blood alcohol concentration, or a compound capable of lowering blood aldehyde concentration. Examples of the other compound having an effect of suppressing elevation of blood alcohol concentration include glycerol, carnitine, caffeine, glycine, maltitol, lactitol, and the like. Meanwhile, examples of the compound capable of lowering blood aldehyde concentration include ethanolamine, pantethine, pantetheine, taurine, and the like.

The agent for suppressing elevation of blood alcohol concentration of the present invention is capable of suppressing elevation of blood alcohol concentration after drinking, when being ingested at any time before, during, or after ingestion of an alcoholic beverage. From the viewpoint of effects, the agent is preferably ingested before or during ingestion of alcoholic beverage.

The ingestion method is not particularly limited, and the agent is orally ingested in the form of an aqueous solution, a tablet, a granule, or the like, for example. Moreover, the agent added to an alcoholic beverage may be ingested. Further, the agent may be added as an additional ingredient during the production of an alcoholic beverage. An appropriate ingestion amount of the agent for suppressing alcohol concentration elevation of the present invention depends on the mass of alcohol contained in the alcoholic beverage ingested. The ingestion amount of the agent by mass is preferably a half or more of the mass of the ingested alcohol. If the amount is less than a half, the effects are weak.

When the agent is added as an additional ingredient during the production of an alcoholic beverage, the agent is preferably added by the following method.

For example, the agent is added to a pre-fermentation liquid obtained after completion of saccharification process, when the agent is added during the production of a beer-taste alcoholic beverage using or not using malt. Meanwhile, the agent is added in the form of an aqueous solution or a carbonated water to Shochu (Japanese distilled alcoholic beverage) or whisky, which serves as a raw material alcohol, when the agent is added during the production of Chuhai (Shochu-based highball) or highball.

EXAMPLES

The present invention will be described in further detail on the basis of Examples. However, the present invention is not limited to these Examples. Note that % represents % by mass, unless otherwise noted.

Example 1

Purified water ($H_2O$), a 40% aqueous dextrin (TK-16) solution, or a 40% aqueous indigestible dextrin (Fibersol 2 (may be abbreviated as FS2)) solution, and the same amount of a 40% aqueous ethanol solution were orally administered by using stomach tubes to 7 to 8-week old Wistar strain male rats fasted for 16 hours. The total amount of the solutions administered was 6 g/kg of body weight, and the blood was collected from the tail vein before the administration (0 minutes) and over time from 30 minutes to 240 minutes after the administration. The blood ethanol concentration was measured by using an ethanol assay kit (F-kit) of Wako Pure Chemical Industries, Ltd. The collected blood was mixed with an 8 fold amount of a 0.33 M ice-cooled perchloric acid, and a supernatant obtained by centrifugation was used for the measurement.

FIG. 1 shows the change of the blood ethanol concentration up to 240 minutes after the administration of each solution. The blood ethanol concentration reached a peak 60 minutes after the administration, and the blood ethanol almost disappeared 240 minutes after the administration. The peak concentration of the FS2 administration group was significantly lowered, and also the concentrations of the FS2 administration group were significantly lowered from 30 minutes to 120 minutes after the administration, as compared with the purified water administration group. On the other hand, the blood ethanol concentrations of the TK-16 administration group were lowered as compared with the purified water administration group, but the suppression of the elevation of the TK-16 administration group up to 60 minutes after the administration was not significant.

Example 2

Purified water ($H_2O$), a 20% aqueous indigestible dextrin (FS2) solution, or a 40% aqueous indigestible dextrin (FS2) solution, and the same amount of a 40% aqueous ethanol solution were orally administered by using stomach tubes to 7 to 8-week old Wistar strain male rats fasted for 16 hours. Table 1 shows the concentration of the indigestible dextrin in each solution administered.

The total amount of the solutions administered was 6 g/kg of body weight. The blood was collected from the tail vein before the administration (0 minutes) and over time from 30 minutes to 240 minutes after the administration. The blood ethanol concentration was measured by using an F-kit. The collected blood was mixed with an 8 fold amount of a 0.33 M ice-cooled perchloric acid, and a supernatant obtained by centrifugation was used for the measurement.

TABLE 1

| Group | Indigestible dextrin concentration (%) |
| --- | --- |
| Purified water ($H_2O$) | 0 |
| 20% FS2 | 10 |
| 40% FS2 | 20 |

Figure 2:
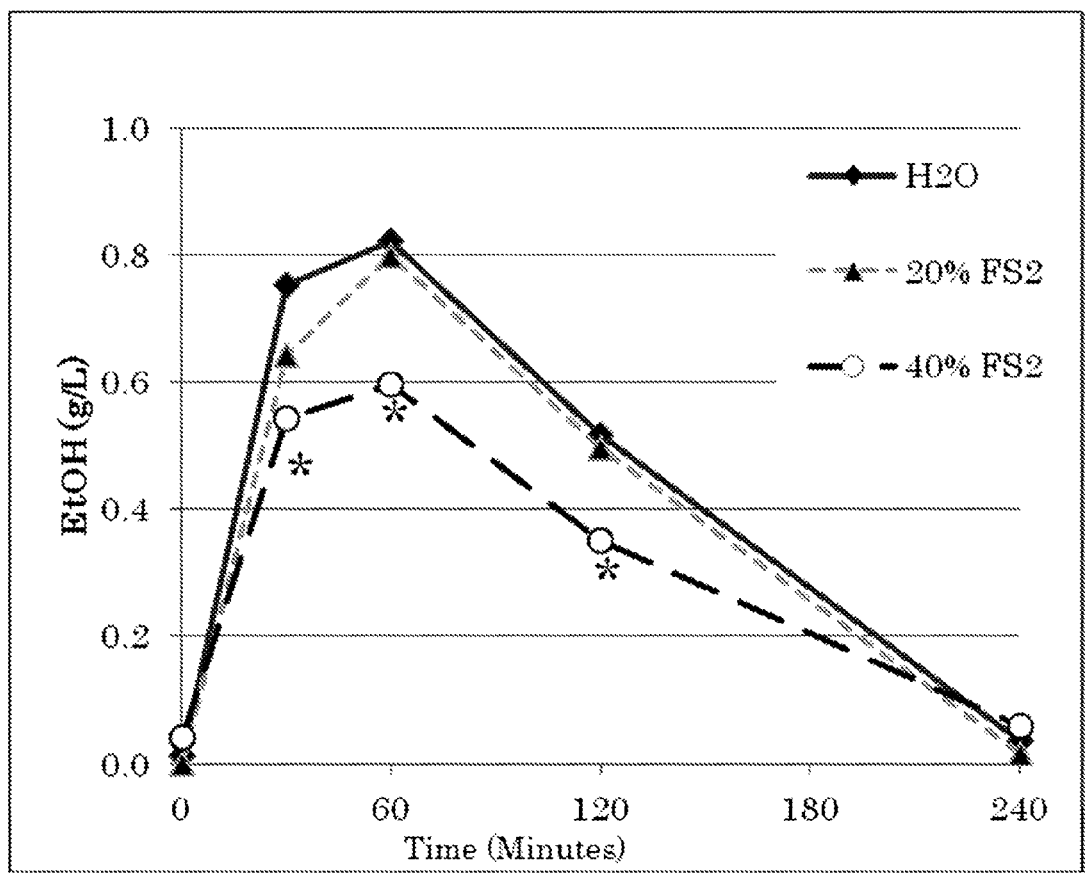
FIG. 2 shows the change in blood ethanol concentration after purified water ($H_2O$), a 20% indigestible dextrin (FS2) solution, or a 40% indigestible dextrin (FS2) solution, and the same amount of a 40% aqueous ethanol solution were administered to rats. * indicates that the value is significant over that of purified water.

FIG. 2 shows the change of the blood ethanol concentration up to 240 minutes after the administration of each solution. The blood ethanol concentration reached a peak 60 minutes after the administration, and the blood ethanol almost disappeared 240 minutes after the administration. The peak concentration of the 40% FS2 administration group was significantly lowered, and also the blood concentrations of the 40% FS2 administration group were significantly lowered from 30 minutes to 120 minutes after the administration, as compared with the purified water administration group. On the other hand, the values of the blood ethanol concentration of the 20% FS2 administration group were lowered up to 30 minutes after the administration as compared with the purified water administration group, but the values and the change of the 20% FS2 administration group after that were almost the same as those of the purified water administration group.

These results indicate that when an indigestible dextrin is administered in an amount which is a half or more of the amount of ethanol ingested, the elevation of blood alcohol is suppressed, and a desirable administration amount is equal to or greater than the amount of ethanol ingested.

The invention claimed is:

1. A method for suppressing elevation of blood alcohol concentration in human, comprising administering to the human before, during or after ingestion of an alcoholic beverage an agent for suppressing elevation of blood alcohol concentration,
    wherein the agent for suppressing elevation of blood alcohol concentration consists of an indigestible dextrin or an aqueous indigestible dextrin solution and the amount of the indigestible dextrin is 0.5 parts by mass or more relative to 1 part by mass of the ingested alcohol.

2. The method according to claim 1, wherein the indigestible dextrin is obtained by degradation of a pyrodextrin with an acid or an amylolytic enzyme,
    wherein the pyrodextrin is obtained by heating a starch to a temperature in the range from 120° C. to 200° C. in the presence of an inorganic acid or an organic acid.

* * * * *